United States Patent
Choung et al.

(10) Patent No.: US 9,925,198 B2
(45) Date of Patent: Mar. 27, 2018

(54) PHARMACEUTICAL COMPOSITION FOR PREVENTING OR TREATING HEARING LOSS, COMPRISING CARBENOXOLONE OR ITS PHARMACEUTICALLY ACCEPTABLE SALTS AS EFFECTIVE COMPOUND

(71) Applicant: AJOU UNIVERSITY INDUSTRY-ACADEMIC COOPERATION FOUNDATION, Suwon-si, Gyeonggi-do (KR)

(72) Inventors: Yun-Hoon Choung, Seoul (KR); Yeon Ju Kim, Suwon-si (KR)

(73) Assignee: AJOU UNIVERSITY INDUSTRY-ACADEMIC CORPORATION FOUNDATION, Suwon-si, Gyeonggi-Do (KR)

( * ) Notice: Subject to any disclaimer, the term of this patent is extended or adjusted under 35 U.S.C. 154(b) by 0 days.

(21) Appl. No.: 15/208,608

(22) Filed: Jul. 13, 2016

(65) Prior Publication Data
US 2017/0014425 A1   Jan. 19, 2017

(30) Foreign Application Priority Data
Jul. 13, 2015   (KR) .................. 10-2015-0098945

(51) Int. Cl.
*A61K 31/56* (2006.01)
*A23L 33/10* (2016.01)
*A61K 31/282* (2006.01)
*A61K 31/555* (2006.01)
*A61K 31/7036* (2006.01)

(52) U.S. Cl.
CPC .............. *A61K 31/56* (2013.01); *A23L 33/10* (2016.08); *A61K 31/282* (2013.01); *A61K 31/555* (2013.01); *A61K 31/7036* (2013.01)

(58) Field of Classification Search
None
See application file for complete search history.

(56) References Cited

FOREIGN PATENT DOCUMENTS

KR   10-1467983 B1   12/2014

*Primary Examiner* — Svetlana M Ivanova
(74) *Attorney, Agent, or Firm* — Revolution IP, PLLC

(57) ABSTRACT

The present invention is related to a pharmaceutical composition and health food for preventing or treating hearing loss, wherein the pharmaceutical composition and health food contain carbenoxolone or its pharmaceutically acceptable salts as an effective component. More particularly, a composition including carbenoxolone or its pharmaceutically acceptable salts as an effective component is provided as a pharmaceutical composition for preventing or treating ototoxic hearing loss due to the carbenoxolone or its pharmaceutically acceptable salts prevent damages on auditory cells from ototoxic drugs such as cisplatin anticancer drugs, and the composition may be used as a drug for treating noise-induced hearing loss and age-related hearing loss, as well as ototoxic hearing loss.

2 Claims, 4 Drawing Sheets

PHARMACEUTICAL COMPOSITION FOR PREVENTING OR TREATING HEARING LOSS, COMPRISING CARBENOXOLONE OR ITS PHARMACEUTICALLY ACCEPTABLE SALTS AS EFFECTIVE COMPOUND

CROSS REFERENCE TO PRIOR APPLICATIONS

This application claims priority to and the benefit of Korean Patent Application No. 10-2015-0098945 filed in the Korean Intellectual Property Office on Jul. 13, 2015, the entire contents of which are incorporated herein by reference.

BACKGROUND

1. Field

One or more embodiments relate to a composition for preventing or treating hearing loss, wherein the composition includes carbenoxolone or its pharmaceutically acceptable salts as an effective component.

2. Description of the Related Art

Hearing loss is a disorder that affects 5% to 20% of the whole population, where the population having hearing loss has increased due to environment pollution and population aging of the modern society. When once-occurred hearing impairment lasts permanently, prevention of the occurrence is important.

Most of hearing loss is caused by environmental factors and genetic factor such as drugs (anticancer agents or antibiotics), noise-induced, traumatic, age-related, and congenital factors, which is mainly caused by damages and death of auditory cells. Although most of studies on the auditory cell damage have been related to noise-induced hearing loss, studies on hearing loss caused by ototoxic drug damage mechanism have been insufficient.

A cisplatin anticancer drug is one of typical ototoxic drugs, which occurs serious side-effects such as hearing impairment and equilibrium function impairment or generates irreversible bilateral sensorineural hearing loss. It has been reported that the cisplatin anticancer drug ototoxicity generates auditory impairment in about 30% of cisplatin-takers, and the auditory impairment occurrence frequency was even higher in children as it is about 50%. However, cisplatin has been widely used due to its excellent anticancer treatment effects.

In this regard, most of studies on a treatment method for preventing hearing loss, where the prevention is induced by a cisplatin anticancer drug, have confirmed ototoxicity reduction effects caused by induction of glutathione increasing antioxidant genes and reduction in reactive oxide hyperactivity by using antioxidizing agents such as Bucillamine, vitamin E, Caffeic acid, or N-acetylcysteine as prevention or treatment method using antioxidant. However, understanding of ototoxic hearing loss is insufficient, and there is no significant prevention drug.

CITATION LIST

Patent Document

Korean Registration Patent No. 10-1467983 (published on Dec. 2, 2014)

SUMMARY

One or more embodiments include a pharmaceutical composition or health food for preventing or treating hearing loss, wherein auditory cells are protected from noise, cell-aging, or ototoxic drugs such as anticancer drugs and antibiotics by providing a composition containing carbenoxolone or its pharmaceutically acceptable salts as an effective component.

Additional aspects will be set forth in part in the description which follows and, in part, will be apparent from the description, or may be learned by practice of the presented embodiments.

According to one or more embodiments, a pharmaceutical composition for preventing or treating hearing loss includes carbenoxolone or its pharmaceutically acceptable salts as an effective component.

According to one or more embodiments, an anticancer drug composition for preventing ototoxic hearing loss includes carbenoxolone or its pharmaceutically acceptable salts as an effective component.

According to one or more embodiments, an antibiotics drug composition for preventing ototoxic hearing loss includes carbenoxolone or its pharmaceutically acceptable salts as an effective component.

Also, according to one or more embodiments, health food for preventing or decreasing hearing loss includes carbenoxolone or its pharmaceutically acceptable salts as an effective component.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
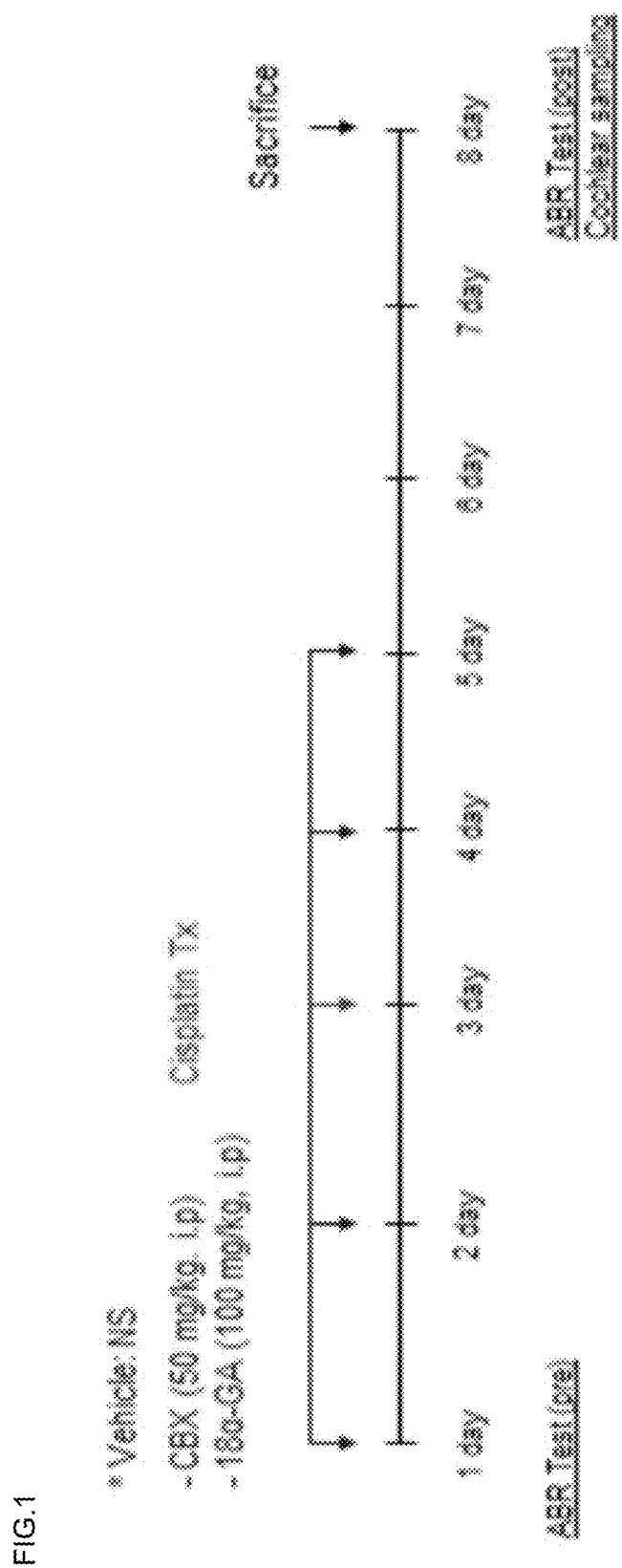
FIG. 1 is a schematic view that illustrates a process of a test for confirming hearing loss prevention effects of carbenoxolone sodium (CBX) in an animal having ototoxic hearing loss induced by cisplatin.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The present invention may provide a pharmaceutical composition for preventing or treating hearing loss, where the composition contains carbenoxolone or its pharmaceutically acceptable salts as an active component.

The carbenoxolone sodium is a component extracted from licorice root, which is a synthetic derivative of glycyrrhizic acid that was conventionally used as an antiulcer agent but, currently, is not being used due to development of novel drugs with better effects.

The hearing loss may be selected from the group consisting of ototoxic hearing loss, noise-induced hearing loss, and age-related hearing loss.

The ototoxic hearing loss may be hearing loss caused by administration of gentamicin, streptomycin, kanamycin, neomycin, amikacin, tobramycin, netilmicin, dibekacin, sisomycin, livodomycin, ciplatin, carboplatin, and oxaliplatin, or, preferably, may be cisplatin, but it is not limited thereto.

Figure 2:
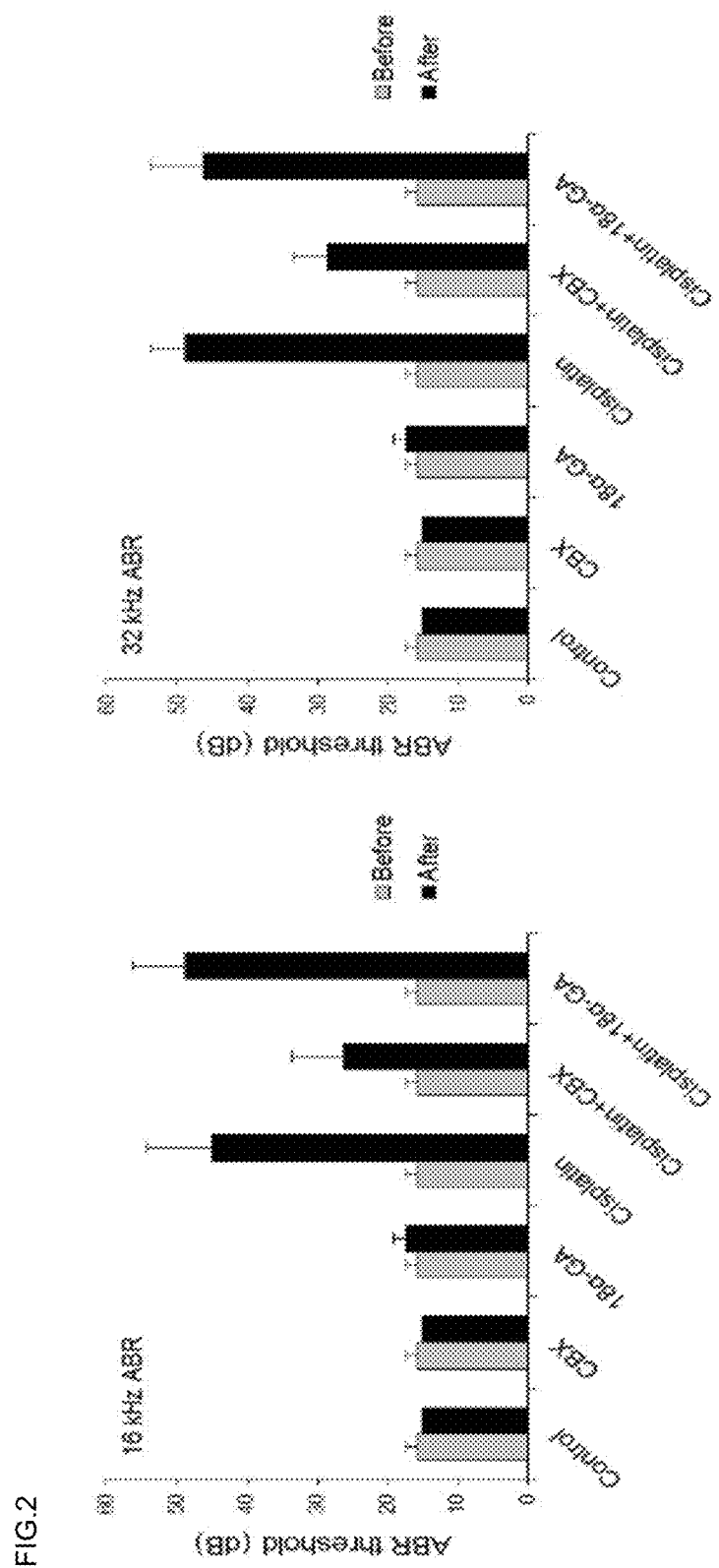
FIG. 2 is the results of an auditory brainstem response (ABR) test performed on rats of each of experiment groups before injecting cisplatin and 5 days after injecting cisplatin at 16 kHz and 32 kHz.

According to one embodiment of the present invention, 50 mg/kg of carbenoxolone sodium (CBX) was administered to rats for 2 days before injecting a cisplatin anticancer drug and 2 days after injecting a cisplatin anticancer drug. As the result, it was confirmed that hearing thresholds increased to 45±9.1 dB at 16 kHz and to 48.8±7.5 dB at 32 kHz in an experimental group to which cisplatin alone was administered as shown in FIG. 2, whereas hearing thresholds decreased to 26.3±7.5 dB at 16 kHz and decreased to 28.8±4.8 dB at 32 kHz in an experimental group to which cisplatin+carbenoxolone sodium was administered as shown in FIG. 2. However, in the case of a cisplatin+18α-GA-treated group-treated group, it was confirmed that hearing thresholds changed to 49.3±4.8 dB at 16 kHz and to 46.2±4.1 dB at 16 kHz, which had no significant difference from those of the cisplatin-administered group. Also, referring to FIG. 4, damages on auditory outer hair cells were observed in numbers in the basal turn (32 kHz) and middle turn (16 kHz) of cochlea of rats administered with cisplatin only, compared to a control group, but as it was statistically confirmed that auditory outer hair cells were significantly preserved in rats administered with cisplatin+carbenoxolone sodium, it may be confirmed that carbenoxolone sodium may prevent auditory cell damage caused by ototoxic drugs.

Thus, the present invention may provide an anticancer drug composition that contains carbenoxolone and its ototoxic anticancer drugs as an effective component and thus may prevent ototoxic hearing loss.

The ototoxic anticancer drug may be selected from the group consisting of cisplatin, carboplatin, and oxaliplatin, but it is not limited thereto.

Also, the present invention may provide an antibiotic composition that contains carbenoxolone and ototoxic antibiotics as an effective component and thus may prevent ototoxic hearing loss.

The ototoxic antibiotics may be selected from the group consisting of gentamicin, streptomycin, kanamycin, neomycin, amikacin, tobramycin, netilmicin, dibekacin, sisomycin, and livodomycin, but it is not limited thereto.

In one embodiment of the present invention, a pharmaceutical composition for preventing or treating hearing loss, wherein the pharmaceutical composition contains carbenoxolone or its pharmaceutically acceptable salts as an effective component, may use one formulation selected from the group consisting of injections, granules, powders, tablets, pills, capsules, suppositories, gel, suspensions, emulsions, drops, and liquid according to a general method.

In another embodiment of the present invention, a pharmaceutical composition for preventing or treating hearing loss, wherein the pharmaceutical composition contains carbenoxolone or its pharmaceutically acceptable salts as an effective component, may further include at least one additive selected from the group consisting of appropriate carriers, excipients, disintegrants, sweeteners, coating agents, swelling agents, lubricants, glidants, flavoring agents, antioxidants, buffers, bacteriostatic agents, diluents, dispersants, surfactants, binders, and lubricants that are generally used in preparation of the pharmaceutical composition.

In particular, carriers, excipients, and diluents may be exemplified by lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oils. Solid preparations for oral administration include tablets, pills, powders, granules, and capsules. These solid preparations are formulated by mixing the composition with at least one excipient, for example, starch, calcium carbonate, sucrose, lactose, and gelatin. Also, in addition to simple excipients, lubricants such as magnesium stearate or talc may be used. Liquid preparations for oral administration include suspensions, solutions, emulsions, or syrups. The liquid preparations may include commonly used, simple diluents such as water and liquid paraffin, and may further include various excipients, for example, humectants, sweeteners, aromatics, and preservatives. Preparations for parental administration include sterilized aqueous solutions, non-aqueous solutions, suspensions, emulsions, freeze-dried preparations, or suppositories. For non-aqueous solutions and suspensions, propylene glycol, polyethylene glycol, vegetable oils such as olive oil, and injectable esters such as ethyloleate may be used. Bases of suppositories may include witepsol, macrogol, tween 61, cacao butter, laurin butter, or glycerogelatin.

According to an embodiment of the present invention, the pharmaceutical composition may be administered to the subject by using a common method through intravenous, intraarterial, intraperitoneal, intramuscular, intrasternal, percutaneous, intranasal, inhalation, topical, rectal, oral, intraocular, or intradermal routes.

The effective dosage of the carbenoxolone or its pharmaceutically acceptable salts can be determined by those in the art according to condition and weight of a patient, type and severity of a disease, type of a drug, administration pathway and duration. According to one embodiment of the present invention, one-day dosage may be, but not limited to, 0.01 to 200 mg/kg, particularly, 0.1 to 200 mg/kg, or, more particularly, 0.1 to 100 mg/kg. The administration frequency may be once a day or a few times a day.

The subject herein may be mammals including humans, but it is not limited thereto.

Also, the present invention may provide health food for preventing or decreasing hearing loss, wherein the health food contains carbenoxolone or its pharmaceutically acceptable salts as an effective component.

The hearing loss may be selected from the group consisting of ototoxic hearing loss, noise-induced hearing loss, and age-related hearing loss, and the ototoxic hearing loss may be hearing loss caused by administration of ototoxic drug such as gentamicin, streptomycin, kanamycin, neomycin, amikacin, tobramycin, netilmicin, dibekacin, sisomycin, livodomycin, cisplatin, carboplatin, or oxaliplatin, or, more preferably, cisplatin, but it is not limited thereto.

The health food may be provided in the form of powder, granules, tablets, capsules, syrup, or beverage. The health food may be used together with other food or food additives in addition to the carbenoxolone or its pharmaceutically acceptable salts according to the present invention as an effective component, or may be appropriately used according to a common method. A mixing amount of the effective component may be suitably determined depending on the purpose of use, for example, for prevention of diseases, for health, or for therapeutic treatment.

The effective dosage of carbenoxolone or its pharmaceutically acceptable salts contained in the health food may be used based on an effective dosage of the pharmaceutical composition. However, in the case of long-term take, the dosage may be used in the above range or less, or even more since the effective component has no problem in terms of safety.

The health food herein is not particularly limited, and examples of the health food may include meat, sausages, bread, chocolates, candies, snacks, cookies, pizza, ramens, noodles, gums, dairy products including ice cream, soups, beverages, tea, drinks, alcohol drinks, and vitamin complex.

Hereinafter, the present invention will now be described in detail with reference the following examples. However, these examples are given for the purpose of illustration and are not to be construed as limiting the scope of the present invention. These embodiments are provided so that this disclosure will be thorough and complete, and will fully convey the scope of the present invention to those skilled in the art.

Example 1

Confirmation of Hearing Loss Prevention Effect of Carbenoxolone Sodium

1. Drug Administration

The total number of 36 rats were classified into (1) a saline solution-treated group, (2) a cisplatin-treated-treated group, (3) a 18α-glycyrrhetinic acid (18α-GA)-treated-treated group, (4) a carbenoxolone sodium-treated-treated group, (5) a cisplatin+18α-GA-treated-treated group, and (6) a cisplatin+carbenoxolone sodium-treated-treated group, each group having 6 rats, and the test was performed as shown in FIG. 1.

0.15 mg/ml of a cisplatin anticancer drug (Sigma-Aldrich) was diluted by using 0.9% saline solution, and 16 mg/kg of the solution was once intraperitoneally injected to a 7-week-old SD-rat. 18α-GA (Sigma-Aldrich) was dissolved in dimethyl sulfoxide (DMSO) at a concentration of 100 mg/kg, and carbenoxolone disodium salt (Sigma-Aldrich) was dissolved in water at a concentration of 50 mg/kg, and these were administered to the rats, daily for 2 days before and after administration of cisplatin, so that each rat was administered with the drugs 4 times in total.

2. Confirmation of Auditory Acuity Change According to Drug Administration

Auditory acuity was evaluated by performing an auditory brainstem response (ABR) test on the SD-rat before and after the drug administration.

The ABR test was determines the minimum stimuli intensity (dB) that evokes the waveform of wave V by providing tone burst of 16 kHz and 32 kHz using a TDT ABR device as a hearing threshold, and the auditory acuities were measured 1 day before the drug administration and 5 days after the drug administration.

As the results shown in FIG. 2, it was confirmed that the hearing thresholds increased to 45±9.1 dB at 16 kHz and to 48.8±7.5 dB at 32 kHz in the case of the cisplatin-treated group-treated group, whereas the hearing thresholds decreased to 26.3±7.5 dB at 16 kHz and decreased to 28.8±4.8 dB at 32 kHz in the case of the cisplatin+carbenoxolone sodium-treated group-treated group. However, in the case of the cisplatin+18α-GA-treated group-treated group, the hearing thresholds increased to 49.3±4.8 dB at 16 kHz and to 46.2±4.1 dB at 32 kHz, which did not show significant difference from the results of the cisplatin-treated group-treated group.

In this regard, it may be confirmed that carbenoxolone sodium may prevent auditory cell damage caused by ototoxic drugs.

3. Confirmation of Cochlea Shape Change According to Drug Administration

Phalloidin staining was performed on auditory sensory hair cell stereocilia markers of the SD-rats administered with drugs by using the method described above to confirm degrees of loss or damage on auditory cells at sites of the basal turn (32 kHz) and the middle turn (16 kHz).

Figure 3:
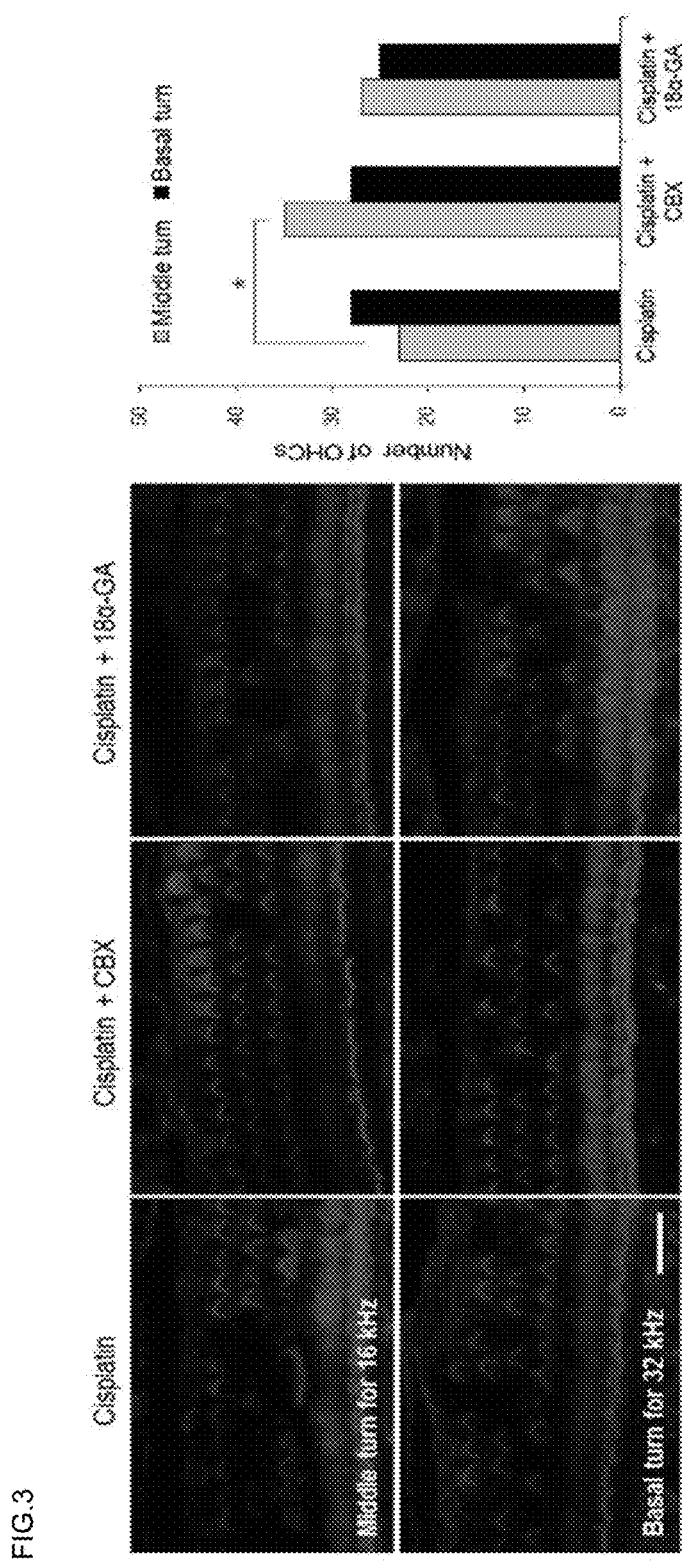
FIG. 3 is the results that confirm a degree of damage on auditory sensory hair cell stereocilia after phalloidin staining. *$P<0.05$ vs cisplatin alone.

As the results shown in FIG. 3, compared to a control group, a number of stereocilia damages were observed at the basal turn (32 kHz) and the middle turn (16 kHz) in the cochlea of the cisplatin-treated group, but it was statistically confirmed that the outer hair cells were significantly preserved in the cisplatin+carbenoxolone sodium-treated group-treated group. On the other hand, damage prevention effect due to 18α-GA was not exhibited in the cisplatin+18α-GA-treated group-treated group.

Also, degrees of loss and damage on auditory cells at the basal turn (32 kHz) and the middle turn (16 kHz) in cochlea were confirmed by using a scanning electron microscope (SEM) to analyze the shape of cochlea.

Figure 4:
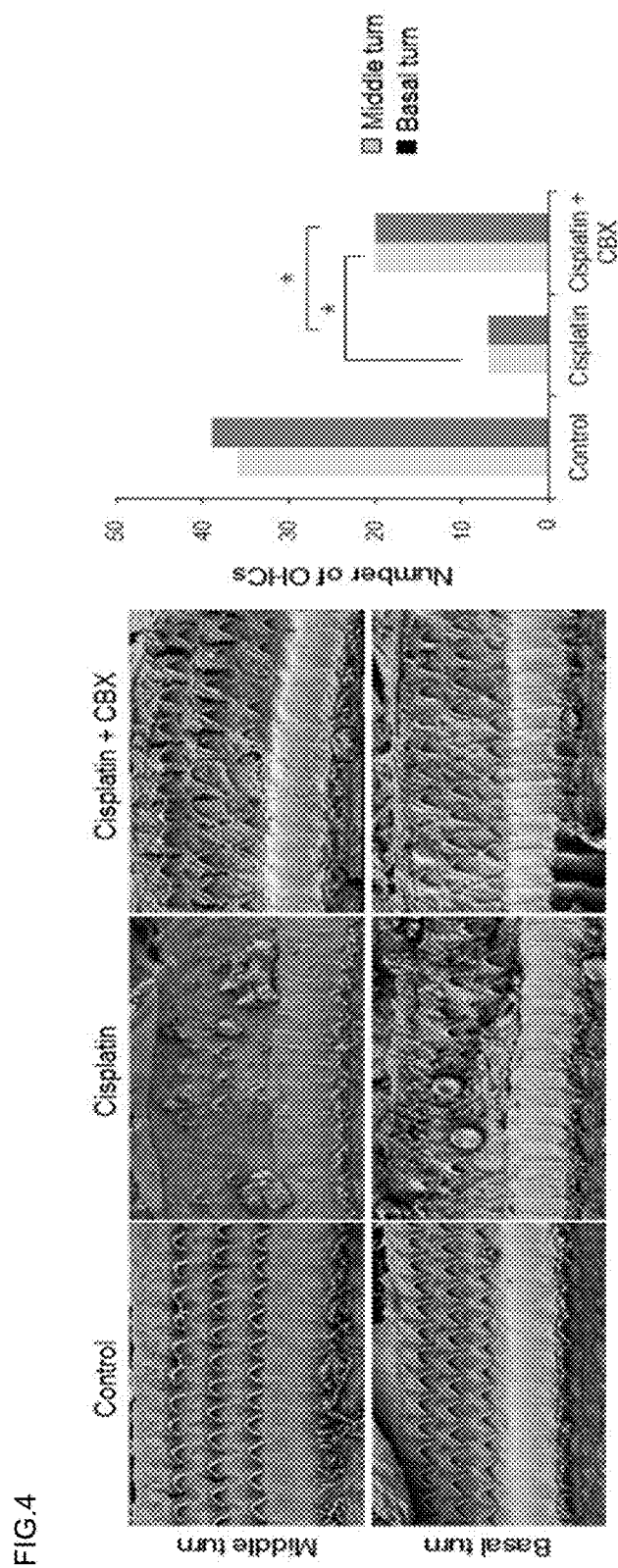
FIG. 4 is the results that confirm a degree of damage on outer hair cell stereocilia at basal turn (32 kHz) and middle turn (16 kHz). *$P<0.05$ vs cisplatin alone.

As the results shown in FIG. 4, compared to the control group, a number of auditory outer hair cell damages were observed at the basal turn (32 kHz) and the middle turn (16 kHz) in the cochlea of the cisplatin-treated group-treated group, whereas it was statistically confirmed that the outer hair cells were significantly preserved in the cisplatin+carbenoxolone sodium-treated group, but the damage prevention effect due to 18α-GA was not confirmed. In this regard, it may be confirmed that carbenoxolone sodium may prevent auditory cell damage caused by ototoxic drugs.

As described above, according to one or more embodiment of the present invention, as it has been confirmed that carbenoxolone or its pharmaceutically acceptable salts exhibits preventing and treating effects on auditory cell damages from ototoxic drugs such as a cisplatin anticancer drug, a composition including carbenoxolone or its pharmaceutically acceptable salts as an effective component may be provided in the form of a pharmaceutical composition or health food for preventing or treating ototoxic hearing loss, and may be used as a treating agent for noise-induced hearing loss or age-related hearing loss as well as ototoxic hearing loss.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of preventing ototoxic hearing loss in a subject in need thereof, comprising:

providing an anticancer drug composition comprising carbenoxolone and ototoxic anticancer drug thereof as an effective component; and administering the anticancer drug composition to the subject, wherein the ototoxic hearing loss is prevented.

2. The method of claim 1, wherein the ototoxic anticancer drug is selected from the group consisting of cisplatin, carboplatin, and oxaliplatin.

* * * * *